(12) United States Patent
Singh et al.

(10) Patent No.: US 12,611,214 B2
(45) Date of Patent: Apr. 28, 2026

(54) OVER THE SCOPE CLIP WITH COMPLIANT MECHANISM

(71) Applicants:BOSTON SCIENTIFIC MEDICAL DEVICE LIMITED, Galway (IE); BOSTON SCIENTIFIC SCIMED, INC., Maple Grove, MN (US)

(72) Inventors: Rajivkumar Singh, Thane (IN); Arun Adhikarath Balan, Aluva (IN); Paul Smith, Smithfield, RI (US)

(73) Assignees: Boston Scientific Medical Device Limited, Galway (IE); Boston Scientific Scimed, Inc., Maple Grove, MN (US)

( * ) Notice: Subject to any disclaimer, the term of this patent is extended or adjusted under 35 U.S.C. 154(b) by 638 days.

(21) Appl. No.: 17/811,704

(22) Filed: Jul. 11, 2022

(65) Prior Publication Data

US 2023/0054185 A1 Feb. 23, 2023

Related U.S. Application Data

(60) Provisional application No. 63/260,325, filed on Aug. 17, 2021.

(51) Int. Cl.
A61B 17/08 (2006.01)
A61B 17/128 (2006.01)

(52) U.S. Cl.
CPC ........ A61B 17/083 (2013.01); A61B 17/1285 (2013.01)

(58) Field of Classification Search
CPC . A61B 17/083; A61B 17/122; A61B 17/1285; A61B 2017/00296
See application file for complete search history.

(56) References Cited

U.S. PATENT DOCUMENTS

| | | | |
|---|---|---|---|
| 8,945,157 | B2 | 2/2015 | Gordon et al. |
| 2003/0069592 | A1 | 4/2003 | Adams et al. |
| 2006/0208028 | A1 | 9/2006 | Kanner |
| 2007/0049967 | A1 | 3/2007 | Sibbitt, Jr. et al. |
| 2014/0228864 | A1* | 8/2014 | Jugenheimer ........ A61B 17/122 606/157 |
| 2020/0397445 | A1 | 12/2020 | Shikhman et al. |
| 2021/0022740 | A1 | 1/2021 | Favreau et al. |

FOREIGN PATENT DOCUMENTS

| | | |
|---|---|---|
| JP | 2004-511275 A | 4/2004 |
| JP | 2005-503231 A | 2/2005 |

* cited by examiner

*Primary Examiner* — Tan-Uyen T Ho
*Assistant Examiner* — Cherie M Poland
(74) *Attorney, Agent, or Firm* — Fay Kaplun & Marcin, LLP

(57) ABSTRACT

A clipping system includes an adapter and a clip. The adapter is mounted over a distal end of an insertion device to a distal end and has a first annular groove formed in a distal face of the adapter. The clip has a body; a central body having a coupling portion and a ring; and jaws having outer arms coupled to the body at an outer arm proximal end and inner arms disposed radially inward of the outer arms and coupled to the ring at an inner arm proximal end. The body includes an annular protrusion extending proximally from a proximal surface of the body. The protrusion is inserted into the first groove of the adapter to couple the clip to the adapter. Movement of the central body along an axis of the clip causes movement of the jaws between an insertion configuration and a deployment configuration.

11 Claims, 3 Drawing Sheets

OVER THE SCOPE CLIP WITH COMPLIANT MECHANISM

PRIORITY CLAIM

The present disclosure claims priority to U.S. Provisional Patent Application Ser. No. 63/260,325 filed Aug. 17, 2021; the disclosure of which is incorporated herewith by reference.

FIELD

The present disclosure relates to endoscopic devices and, in particular, relates to endoscopic clipping devices for treating tissue.

BACKGROUND

Physicians have become more willing to perform aggressive interventional and therapeutic endoscopic gastrointestinal (GI) procedures, which may increase the risk of perforating the wall of the GI tract or may require closure of the GI tract wall as part of the procedure. Such procedures may include, for example, the removal of large lesions, tunneling under the mucosal layer of the GI tract to treat issues below the mucosa, full thickness removal of tissue, treatment of issues on other organs by passing outside of the GI tract, and endoscopic treatment/repair of post-surgical issues (e.g., post-surgical leaks, breakdown of surgical staple lines, and anastomotic leaks).

Currently, tissue may be treated via endoscopic closure devices including through-the scope clips or over-the-scope clips. Over-the-scope clips may be particularly useful for achieving closure of larger tissue defects. These endoscopic closure devices can save costs for the hospital and may provide benefits for the patient. In some cases, however, current endoscopic closure devices may be difficult to use, time consuming to position, or insufficient for certain perforations, conditions and anatomies.

SUMMARY

The present disclosure relates to a clipping system for treating tissue which includes an adapter extending longitudinally from a proximal end configured to be mounted over a distal end of an insertion device to a distal end. The adapter has a first annular groove formed in a distal face of the adapter. The system also has a clip including (i) a body, (ii) a central body having a coupling portion and a ring, and (iii) first and second jaws having outer arms coupled to the body at an outer arm proximal end and inner arms disposed radially inward of the outer arms and coupled to the ring at an inner arm proximal end. The body includes an annular protrusion extending proximally from a proximal surface of the body. The annular protrusion is configured to be inserted into the first annular groove of the adapter to couple the clip to the adapter. Movement of the central body along an axis of the clip causes movement of the first and second jaws between an insertion configuration, in which the first and second jaws are separated from one another to receive tissue therebetween, and a deployment configuration, in which the first and second jaws are drawn toward one another to grip tissue therebetween.

In an embodiment, the clip is a monolithic structure formed of a compliant material.

In an embodiment, the compliant material is Nitinol.

In an embodiment, the first and second jaws are biased towards the insertion configuration.

In an embodiment, the proximal movement of the central body is configured to cause a corresponding proximal movement of the inner arms and to bend the outer arms inwardly towards the deployment configuration.

In an embodiment, the body of the clip includes a second annular groove configured to receive the ring when the clip is in the deployment configuration.

In an embodiment, a first diameter of a distalmost portion of the second annular groove is less than a second diameter of the ring, and wherein the ring is configured to snap into the second annular groove after being forced proximally beyond the distalmost portion of the second annular groove.

In addition, the present disclosure relates to a clipping system for treating tissue which includes an endoscope including a shaft extending longitudinally from a proximal end to a distal end and a wire extending from the proximal end to the distal end, wherein the wire includes an enlarged portion at a distal end of the wire; an adapter including a proximal portion mounted over the distal end of the shaft of the endoscope and a distal portion extending distally from the proximal portion; and a clip including (i) a body, (ii) a central body having a coupling portion and a ring, and (iii) first and second jaws having outer arms coupled to the body at an outer arm proximal end and inner arms disposed radially inward of the outer arms and coupled to the ring at an inner arm proximal end. The body includes an annular protrusion extending proximally from a proximal surface of the body, the annular protrusion configured to be inserted into the first annular groove of the adapter to couple the clip to the adapter. The wire extends through an opening formed in the coupling portion such that the enlarged portion of the wire is distal to the opening. A diameter of the opening is smaller than a diameter of the enlarged portion of the wire. Movement of the wire proximally and distally causes a corresponding movement of the central body along an axis of the clip. Movement of the central body along the axis of the clip causes movement of the first and second jaws between an insertion configuration, in which the first and second jaws are separated from one another to receive tissue therebetween, and a deployment configuration, in which the first and second jaws are drawn toward one another to grip tissue therebetween.

In an embodiment, the clip is a monolithic structure formed of a compliant material.

In an embodiment, the compliant material is Nitinol.

In an embodiment, the first and second jaws are biased towards the insertion configuration. Movement of the wire proximally causes the enlarged portion of the wire to abut against the coupling portion, the coupling portion to move proximally, and the first and second jaws to move towards the deployed configuration. Release of the wire allows the first and second jaws to return to the insertion configuration.

In an embodiment, the proximal movement of the central body is configured to cause a corresponding proximal movement of the inner arms and to bend the outer arms inwardly towards the deployment configuration.

In an embodiment, the body of the clip includes a second annular groove configured to receive the ring when the clip is in the deployment configuration.

In an embodiment, a first diameter of a distalmost portion of the second annular groove is less than a second diameter of the ring, and wherein the ring is configured to snap into the second annular groove after being forced proximally beyond the distalmost portion of the second annular groove.

Furthermore, the present disclosure relates to a method for treating tissue which includes inserting a clip to a target area in a body lumen via an endoscope, the clip mounted over a distal end of an endoscopic shaft, via an adapter, in an open insertion configuration in which jaws of the clip are separated from one another, wherein a body of the clip couples the clip to the adapter; inserting a tissue grasper through a working channel of the endoscope and through the clip so that tissue is drawn into a space between jaws of the clip; retracting a wire passing through the working channel and through the clip proximally, the wire having an enlarged portion at a distal end of the wire that engages a coupling portion of the clip to cause a corresponding proximal motion of the coupling portion, wherein proximal movement of the coupling portion causes a corresponding proximal movement of a ring of the clip which is connected to the coupling portion, wherein the ring is coupled to proximal ends of inner arms of the jaws and proximal movement of the ring causes a corresponding proximal movement of the inner arms, wherein the jaws include outer arms disposed radially outward of the inner arms, the outer arms coupled to the body of the clip at proximal ends of the outer arms and to the inner arms at distal ends of the outer arms, and wherein proximal motion of the inner arms pulls the distal ends of the outer arms together from an insertion configuration in which the jaws are separated from one another towards a deployed configuration in which the jaws close toward one another to grip the tissue received therebetween; retracting the wire further proximally to force the ring into a corresponding annular groove formed in a body of the clip, the annular groove configured to retain the ring therein and maintain the clip in the deployed configuration; and retracting the wire further to break off the enlarged portion of the wire and allow the clip to be separated from the adapter.

In an embodiment, the clip is a monolithic structure formed of a compliant material.

In an embodiment, the jaws are biased towards the insertion configuration.

BRIEF DESCRIPTION

DETAILED DESCRIPTION

Figures 1, 2A, 2B:
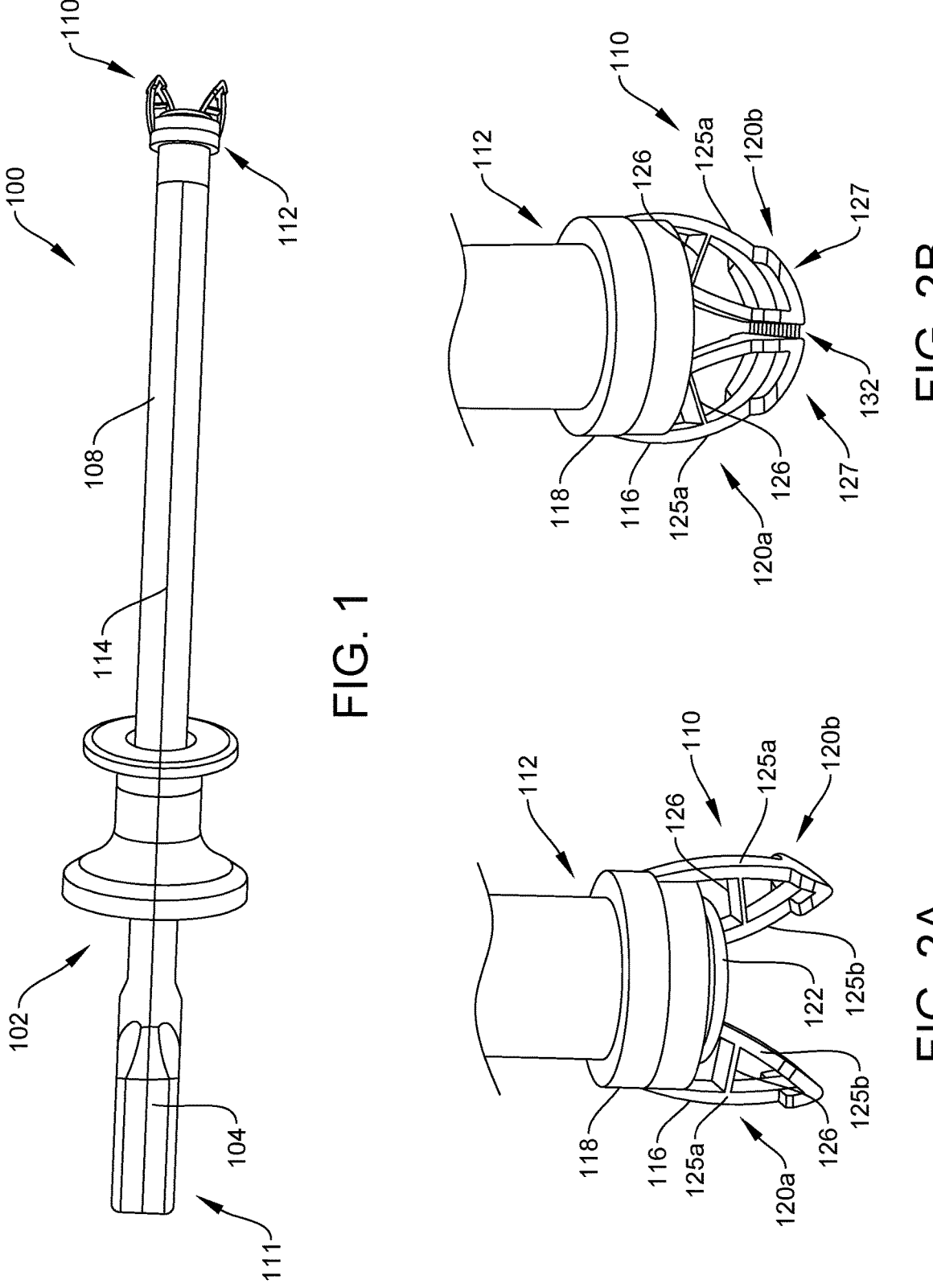
FIG. 1 shows a perspective view of a system according to an exemplary embodiment of the present disclosure.
FIG. 2A shows a longitudinal side view of a distal portion of the system of FIG. 1, in an insertion configuration.
FIG. 2B shows another longitudinal side view of the distal portion of the system of FIG. 1, in a deployed configuration.

The present disclosure may be further understood with reference to the following description and the appended drawings, wherein like elements are referred to with the same reference numerals. The present disclosure relates to a clipping system and, in particular, relates to an over-the-scope endoscopic clipping system, in which an initial placement of a clip may be viewed and adjusted prior to a final deployment thereof. Exemplary embodiments of the present disclosure comprise a clip mountable over a distal end of an endoscope via an adapter and having jaws that may be moved between an insertion configuration and a deployed configuration.

A clip according to the disclosed embodiments is mounted on the distal end of an endoscope or other insertion instrument via an adapter that is slid over the end of the endoscope and maintained on the endoscope via a friction fit. The clip is seated in the adapter and extends around the distal end of the endoscope with two tissue clipping jaws extending distally beyond the distal end of the endoscope. The jaws of the clips according to the disclosed embodiments are biased towards an insertion configuration, in which the jaws of the clip are spread apart from one another to receive tissue to be clipped.

A radially inner proximal portion of each of the jaws is coupled to a ring of a central body which engages a wire that moves the ring proximally and distally to move the jaws between the insertion configuration and a deployed configuration in which they are drawn together to clip tissue. Movement of the wire proximally draws the central body proximally, which draws the radially inner proximal portion of each jaw proximally closing the jaws. Releasing the wire allows the jaws to spread apart under their natural bias into the insertion configuration. This pulls the radially inner proximal portions of the jaws distally drawing the ring and wire distally. This permits a user to position the clip relative to target tissue to be clipped with the clip in the insertion configuration.

The user may then draw a portion of tissue between the jaws and draw the jaws toward the deployed configuration while observing the jaws and the tissue gripped by the jaws using the vision system of the endoscope. If the proper tissue is not gripped or the tissue is not gripped as desired, the user may release the control wire to reopen the clip. This releases the gripped tissue so that the device may be repositioned and until the desired portion of tissue is located between the jaws. When the tissue is observed to be located between the jaws as desired, the control wire may be drawn proximally to draw the clip to a fully deployed configuration in which the jaws are locked closed over the clipped tissue as will be described in more detail below.

The clip includes a groove configured to receive the ring of the central body such that movement of the wire proximally beyond a predetermined distance snaps the ring into the groove preventing the ring from moving distally even if the control wire is released. This locks the jaws in the deployed configuration clipped over the tissue. The control wire passes through an opening in a cross member coupled to the ring with an enlarged portion at the distal end of the control wire engaging the surface of the cross member surrounding the opening so that drawing the control wire proximally draws the cross member and the ring proximally to close the jaws.

When the ring is snapped into the groove, applying tension to the control wire does not generate further movement of the control wire proximally. When this tension exceeds a predetermined level, the enlarged end breaks off from the rest of the control wire. At this point the clip is connected to the endoscope only by an interface between the clip and the adapter. The clip can now be completely separated from the endoscope and the adapter by simply withdrawing the endoscope proximally so that the connection between the clip and the clipped tissue pulls the clip free from the adapter. The endoscope and the adapter can now be removed from the body leaving the clip in place clipped over the target tissue as will be described in more detail below.

Specifically, as shown in FIGS. 1-3C, a clipping system 100 for treating tissue defects and/or perforations according to an exemplary embodiment comprises a clip assembly 110 having a clip 116 coupled to an adapter 118. The adapter 118 with the clip 116 coupled thereto configured to be mounted over the distal end of an endoscope 102. Those skilled in the art will understand that the clip 116 and adapter 118 may be made in different sizes and shapes to accommodate different models of endoscopes. In addition, the clip 116 and adapter 118 may be sized and shaped to accommodate any other type of flexible or rigid insertion device. The adapter 118 is slid over a distal end 112 of an endoscopic shaft 108 of the endoscope 102 and maintained on the shaft 108 via, for example, a friction fit. The clip 116 is seated on the distal end of the adapter 118 so that the jaws 120a, b extend distally beyond the distal end of the shaft 108. as seen in FIG. 1. The clip 116 is movable between an insertion configuration (FIGS. 2A and 3A), in which the jaws 120a, b of the clip 116 are separated from one another to receive tissue therebetween, and an initial deployed configuration (FIGS. 2B and 3C), in which the jaws 120a, b of the clip 116 are closed to grip tissue that has been drawn into the clip 116. In the initial deployed configuration, the jaws 120a, b are closed or partially closed but are free to be reopened if it is desired to reposition the clip 116. Each of the jaws 120a, b includes optional gripping features 132 such as, for example, teeth or a roughened surface, for gripping target tissue therebetween as would be understood by those skilled in the art.

The clip 116 includes a body 305 having an annular protrusion 302 (FIGS. 3B and 3C) extending proximally from a proximal surface 304 of the body 305. The annular protrusion 302 is configured to be inserted into a corresponding annular groove 306 formed in a distal surface 308 of the adapter 118 to releasably couple the clip 116 to the adapter 118. In one embodiment, the adapter 118 and the clip 116 are fitted to one another so that the clip 116 is freely rotatable with respect to the adapter 118. This ensures that a deployed clip is not inadvertently rotated if, during removal of the endoscope 102, the endoscope 102 is rotated. Thus, any torque applied to the endoscope 102 is not transmitted to the clip 116 and the clipped tissue.

The clip 116 in this embodiment is a monolithic structure formed of a compliant material and is biased towards the insertion configuration with the jaws 120a, b separated to accept tissue. Such a compliant material may include, for example, plastic, Nitinol, a compliant metal, etc. Those skilled in the art will recognize that the clip 116 may be formed as a unitary whole or may be composed of separate elements joined to one another via, for example, welding. Each of the jaws 120a, b of the clip 116 includes an outer arm 125a and an inner arm 125b disposed radially inward with respect to the outer arm 125a. Each of the outer arms 125a of the jaws 120a, b extends from a proximal end coupled to the body 305 to a distal end that terminates at the gripping features 132. Each of the inner arms 125b of the jaws 120a, b extends from a proximal end coupled to a ring 122 of a central body 121 to a distal end that also terminates at the gripping features 132.

The outer and inner arms 125a, b are coupled at their distal ends at the gripping features 132. Each of the jaws 120a, b includes a supporting element 126 that extends between the outer arm 125a and the inner arm 125b. Each of the outer and inner arms 125a, b includes a distal portion 127 (FIG. 2B) having an increased width proximate the gripping features 132 to increase a gripping area of the gripping features 132.

Figure 3A:
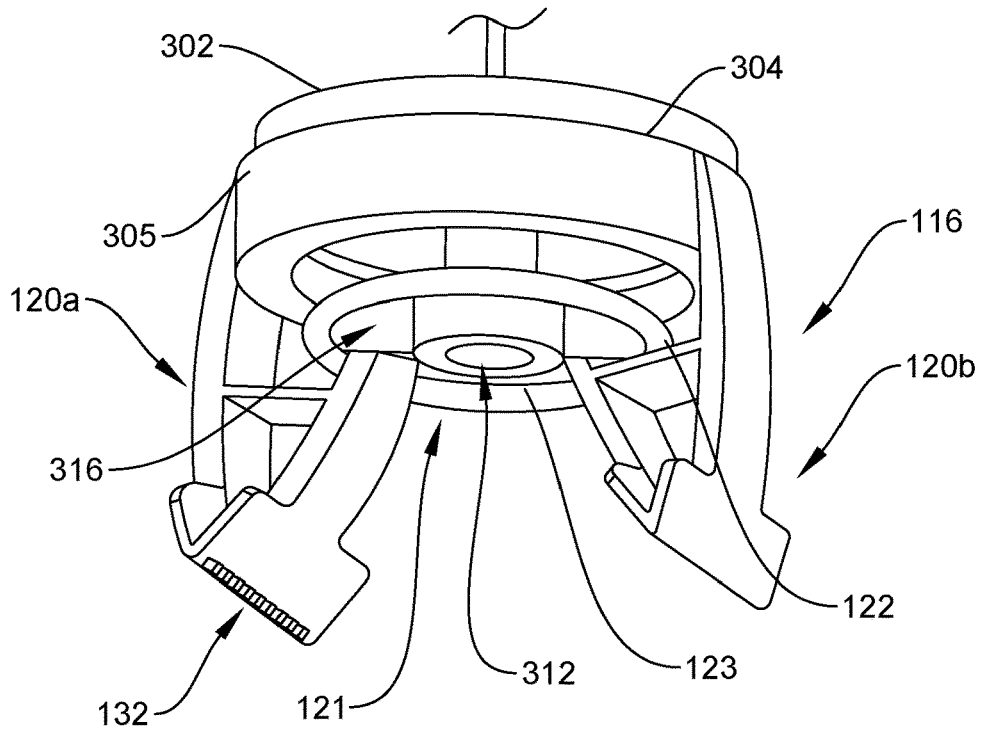
FIG. 3A shows a longitudinal side view of a clip according to an exemplary embodiment of the present disclosure, in an insertion configuration.
Figure 3B:
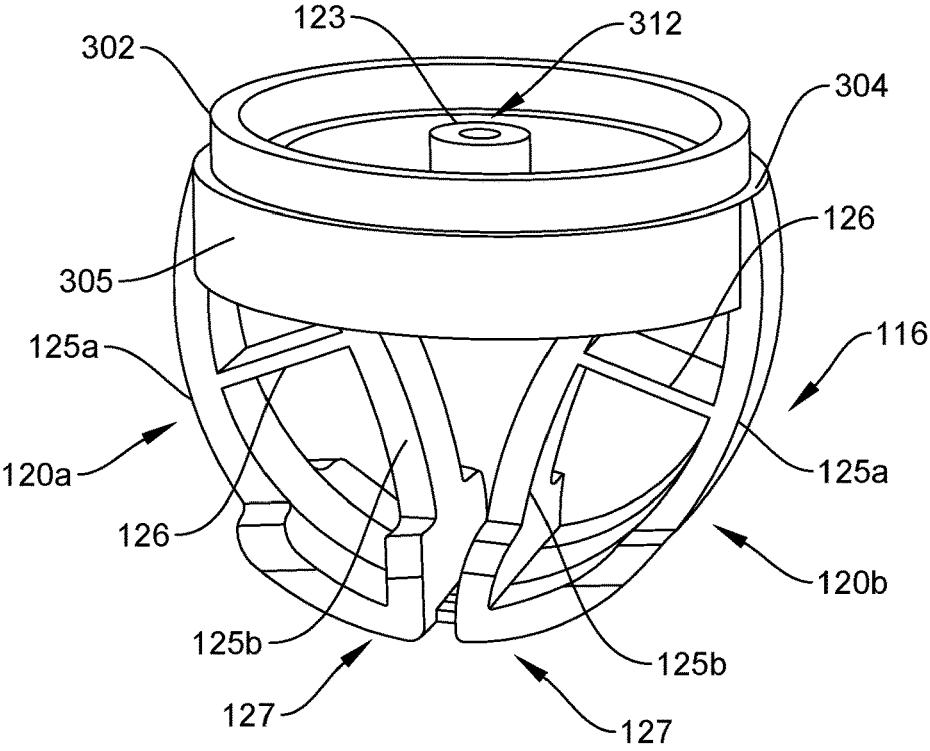
FIG. 3B shows another longitudinal side view of the clip of FIG. 3A, in a deployed configuration.
Figure 3C:
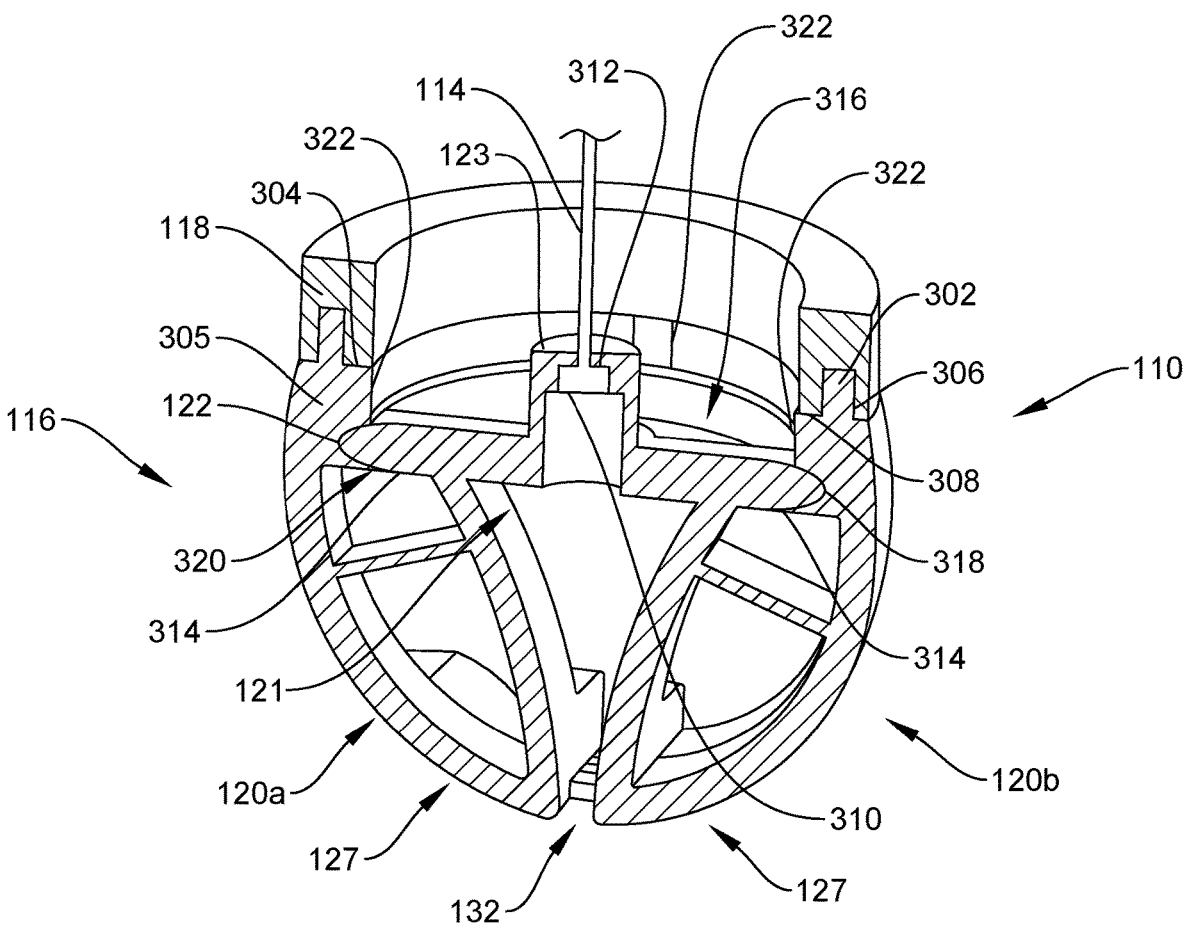
FIG. 3C shows a cross-sectional view of the clip of FIG. 3A, in a deployed configuration.

The inner arms 125b are coupled to the central body 121 so that movement proximally or distally of the central body 121 draws the inner arms 125b proximally and distally causing the jaws 120a, b to move toward and away from one another so that the clip transitions between the insertion configuration and the deployed configuration. Because the body 305 does not move, there is no proximal or distal motion of the proximal ends of the outer arms 125a. However, as the inner arms 125b are moved proximally due to movement of the ring 122, the distal ends of the outer arms 125a are flexed inwardly so that the distal ends of the arms 125a come together into the deployed configuration as shown in FIGS. 3B and 3C. When the central body 121 is moved distally, the inner arms 125b are pushed distally allowing the outer arms 125a to return to their initial shape with the distal ends of the jaws 120a, b separated from one another in the insertion configuration. The supporting element 126 is configured to maintain a distance between the outer and inner arms 125a, b as the outer arms 125a are flexed and to bias the jaws 120a, b toward the insertion configuration.

To control the movement of the central body 121, a control wire 114 extends from a handle portion 104 distally to the clip assembly 110 and engages a coupling portion 123 of the central body 121. The control wire 114 passes through an opening 312 formed in the coupling portion 123 and includes an enlarged portion 310 (FIG. 3C) at a distal end of the control wire 114. The enlarged portion 310 has a diameter larger than the opening 312 and is disposed distal to the opening 312 such that the enlarged portion cannot be moved proximally through the opening 312. The coupling portion 123 is coupled to the ring 122 via one or more ribs 314 which extend radially outward from the coupling portion 123 to the ring 122. Movement of the control wire 114 proximally presses the enlarged portion 310 against the coupling portion 123 pulling the central body 121 proximally relative to the adapter 118, closing the jaws 120a, b as described above.

Because the jaws 120a, b of the clip 116 are biased toward the open position (the insertion configuration), releasing the wire 114 allows the jaws 120a, b to return to their biased open position. As described above, the operator can maneuver the endoscope 102 to position the clip 116 adjacent to target tissue to be clipped. The operator may then draw tissue into the space between the jaws 120a, b (e.g., by applying suction or a grasping tool through a working channel of the endoscope 102) and partially close the jaws 120a, b while visualizing the clip and the clipped tissue using the vision system of the endoscope 102. If the operator determines that the clip 116 is not properly positioned, the operator releases the control wire 114 permitting the clip 116 to reopen and releasing the tissue.

The endoscope 102 may then be re-positioned and this process may be repeated until the operator observes that the desired tissue is properly gripped between the partially closed jaws 120a, b. At this point, the operator applies further tension to the control wire 114 (e.g., utilizing an actuator on the handle portion 104) until the predetermined tension is reached at which the enlarged portion separates from the rest of the control wire 114. This frees the clip 116 from the control wire 114 and locks the clip 116 closed over the clipped tissue. The operator may then withdraw the endoscope 102 proximally separating the clip 116 from the adapter 118 and the endoscope 102 so that the endoscope 102 and the adapter 118 may be removed from the body while leaving the clip 116 in place clipped to the target tissue.

As discussed above, in one embodiment the clip 116 is mounted to an endoscope 102 via an adapter 118. The adapter 118 is, in this embodiment, sized and shaped to be mounted on the distal end 112 of the endoscopic shaft 108 of a standard endoscope 102 although, as would be understood by those skilled in the art, the adapter 118 may be sized and shaped to be mounted over the distal end of any insertion device (flexible or rigid) suitable for accessing a target site within a body at which tissue to be clipped is located. The adapter 118 in this embodiment is a substantially tubular structure sized and shaped to be mounted over the distal end of an endoscope. The adapter 118 includes a channel extending therethrough which, when the adapter 118 is mounted over the endoscope is substantially aligned with a longitudinal axis of the endoscope so that, when the adapter 118 is mounted on the distal end of the endoscope, the channel extends away from the distal end of the endoscope so that occlusion of the field of view of an optical system of the endoscope is minimized. In one embodiment, the adapter 118 is substantially circular in cross-section to match a similar shape of the endoscope.

As would be understood by those skilled in the art, however, if the endoscope is non-circular (e.g., oval) the adapter may be sized and shaped accordingly to provide, for example, a friction fit with the distal end of the endoscope. The central body 121 in this embodiment includes one or more spaces 316 disposed between the coupling portion 123 and the ring 122 to allow for the passing of tools such as, for example, a tissue grasper. The one or more spaces 316 are configured to minimize occlusion of the field of view of the optical system of the endoscope.

The proximal end 111 of the endoscopic shaft 108 in this embodiment includes a handle portion 104 which may be used by a physician or other user, to guide the flexible endoscope through, for example, a bodily lumen (e.g., gastrointestinal tract) to a target site adjacent to target tissue to be clipped. As would be understood by those skilled in the art, the endoscopic shaft 108 in this embodiment is sufficiently flexible to be inserted through even tortuous paths of the bodily lumen and thus, all of the components of this system that are extended through or along the endoscope to the clip 116 are also sufficiently flexible to permit this insertion to the target site.

The body 305 of the clip 116 in this embodiment includes an annular groove 318 configured to lockingly receive the ring 122 when the clip 116 is in the deployed configuration. When the control wire 114 is moved proximally beyond a certain point, the ring 122 is forced into the annular groove 318. The annular groove 318 includes a reduced diameter portion 320 at its distalmost end having a diameter less than that of the diameter of the ring 122. Because the clip 116 is formed of a compliant material, the ring 122 may be forced past the reduced diameter portion 320 to snap into the annular groove 318 locking the ring 122 into the groove 318. As a result of the ring 122 being fixed in the annular groove 318, the jaws 120a, b are locked in the deployed configuration. To ensure that further proximal movement of the control wire 114 does not cause the ring 122 to move further proximally than the annular groove 318, one or more stops 322 (three shown in FIG. 3C) are disposed adjacent to the annular groove 318 and extend radially inwardly from an inner surface of the clip 116 proximal to the annular groove 318.

The one or stops 322 serve as a hard stop to prevent the ring 122 from moving further proximally than the annular groove 318. As a result, after the ring 122 is snapped into the annular groove 318, further proximal movement of the control wire 114 is prevented and additional tension applied to the control wire 114 eventually rises to a level that separates the enlarged portion 310 from the rest of the control wire 114 freeing the clip 116 to be separated from the adapter 118. The endoscope 102 and the adapter 118 may subsequently be removed, leaving behind the deployed clip 116. The operator may use an actuating device in the handle portion 104 to control the movement of the wire 114 as desired.

It will be apparent to those skilled in the art that various modifications may be made in the present disclosure, without departing from the scope of the disclosure. Furthermore, those skilled in the art will understand that the features of any of the various embodiments may be combined in any manner that is not inconsistent with the description and/or the functionality of the embodiments.

What is claimed is:

1. A clipping system for treating tissue, comprising:
an adapter extending longitudinally from a proximal end configured to be mounted over a distal end of an insertion device to a distal end, the adapter having a first annular groove formed in a distal face of the adapter; and
a clip including (i) a body, (ii) a central body having a coupling portion and a ring, and (iii) first and second jaws having outer arms coupled to the body at an outer arm proximal end and inner arms disposed radially inward of the outer arms and coupled to the ring at an inner arm proximal end,
wherein the body includes an annular protrusion extending proximally from a proximal surface of the body, the annular protrusion configured to be inserted into the first annular groove of the adapter to couple the clip to the adapter, and
wherein movement of the central body along an axis of the clip causes movement of the first and second jaws between an insertion configuration, in which the first and second jaws are separated from one another to receive tissue therebetween, and a deployment configuration, in which the first and second jaws are drawn toward one another to grip tissue therebetween.

2. The system of claim 1, wherein the clip is a monolithic structure formed of a compliant material.

3. The system of claim 2, wherein the compliant material is Nitinol.

4. The system of claim 2, wherein the first and second jaws are biased towards the insertion configuration.

5. The system of claim 4, wherein proximal movement of the central body is configured to cause a corresponding proximal movement of the inner arms and to bend the outer arms inwardly towards the deployment configuration.

6. The system of claim 2, wherein the body of the clip includes a second annular groove configured to receive the ring when the clip is in the deployment configuration.

7. The system of claim 6, wherein a first diameter of a distalmost portion of the second annular groove is less than a second diameter of the ring, and wherein the ring is configured to snap into the second annular groove after being forced proximally beyond the distalmost portion of the second annular groove.

8. The system of claim 6, wherein the body of the clip includes at least one stop extending radially inward from an inner surface of the clip proximal of the second annular groove, the stop configured to prevent the ring from moving further proximally past the second annular groove to lock the clip in the deployment configuration.

9. The system of claim 1, wherein the first and second jaws include gripping features configured to grip tissue therebetween.

10. The system of claim 1, wherein the clip is configured to rotate about an axis relative to the adapter.

11. The system of claim 1, wherein each of the outer and inner arms include a distal portion having an increased width to increase a gripping area of the first and second jaws.

\* \* \* \* \*